(12) United States Patent
Yuan et al.

(10) Patent No.: US 10,716,741 B1
(45) Date of Patent: *Jul. 21, 2020

(54) ORAL CARE COMPOSITIONS AND METHODS FOR THE SAME

(71) Applicant: COLGATE-PALMOLIVE COMPANY, New York, NY (US)

(72) Inventors: Shaotang Yuan, East Brunswick, NJ (US); Paloma Pimenta, Staten Island, NY (US); Cajetan Dogo-Isonagie, Highland Park, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/232,900

(22) Filed: Dec. 26, 2018

(51) Int. Cl.
| | |
|---|---|
| *A61K 8/22* | (2006.01) |
| *A61K 8/23* | (2006.01) |
| *A61K 8/86* | (2006.01) |
| *A61K 8/81* | (2006.01) |
| *A61Q 11/00* | (2006.01) |

(52) U.S. Cl.
CPC .................. *A61K 8/22* (2013.01); *A61K 8/23* (2013.01); *A61K 8/8135* (2013.01); *A61K 8/8182* (2013.01); *A61K 8/86* (2013.01); *A61Q 11/00* (2013.01); *A61K 2800/42* (2013.01); *A61K 2800/872* (2013.01); *A61K 2800/874* (2013.01)

(58) Field of Classification Search
CPC ........................................................ A61K 7/16
USPC ........................................................... 424/53
See application file for complete search history.

(56) References Cited

U.S. PATENT DOCUMENTS

| | | | |
|---|---|---|---|
| 2006/0045854 A1* | 3/2006 | Zaidel | A61K 8/0208 424/53 |
| 2007/0138674 A1 | 6/2007 | Anastasiou et al. | |
| 2008/0050398 A1 | 2/2008 | Bockmuehl et al. | |
| 2008/0260660 A1 | 10/2008 | Engelbrecht et al. | |
| 2009/0175917 A1 | 7/2009 | Engelbrecht et al. | |
| 2014/0377194 A1 | 12/2014 | Strand et al. | |
| 2018/0360708 A1 | 12/2018 | Dogo-Isonagie et al. | |

FOREIGN PATENT DOCUMENTS

| | | | | |
|---|---|---|---|---|
| WO | 00/09079 A1 | | 2/2000 | |
| WO | WO2000/16737 | * | 3/2000 | ............... A61K 7/20 |
| WO | 2018/093357 | | 5/2018 | |

* cited by examiner

*Primary Examiner* — Walter E Webb

(57) ABSTRACT

Oral care compositions and methods for whitening teeth are provided. The oral care composition may include an orally acceptable vehicle, a whitening booster, and a source of hydrogen peroxide. The whitening booster may be dispersed in the orally acceptable vehicle. The whitening booster may include a salt of a monopersulfate, such as an alkali metal salt of the monopersulfate.

10 Claims, No Drawings

ORAL CARE COMPOSITIONS AND METHODS FOR THE SAME

BACKGROUND

Conventional oral care products including whitening agents are often utilized to whiten teeth. For example, conventional oral care products including peroxides, such as hydrogen peroxide, are often utilized to oxidize chromophores bound to surfaces and/or dentin of teeth to thereby whiten the teeth. While oral care products including hydrogen peroxide have proven to be effective for whitening teeth, the utilization of hydrogen peroxide is limiting. For example, increasing concentrations of hydrogen peroxide to improve whitening may often lead to irritation of the teeth and gums. Further, peroxides in oral care products are often highly reactive and prone to decomposition, thereby reducing the whitening efficacy thereof.

What is needed, then, are improved oral care products and whitening compositions thereof, and methods for the same.

BRIEF SUMMARY

This summary is intended merely to introduce a simplified summary of some aspects of one or more implementations of the present disclosure. Further areas of applicability of the present disclosure will become apparent from the detailed description provided hereinafter. This summary is not an extensive overview, nor is it intended to identify key or critical elements of the present teachings, nor to delineate the scope of the disclosure. Rather, its purpose is merely to present one or more concepts in simplified form as a prelude to the detailed description below.

The foregoing and/or other aspects and utilities embodied in the present disclosure may be achieved by providing an oral care composition including an orally acceptable vehicle, a whitening booster, and a source of hydrogen peroxide. The whitening booster may be dispersed in the orally acceptable vehicle, and may include a salt of a monopersulfate.

In at least one implementation, the salt of the monopersulfate may be an alkali metal salt of the monopersulfate.

In at least one implementation, the whitening booster may include potassium monopersulfate.

In at least one implementation, the whitening booster may consist essentially of the salt of the monopersulfate. In another implementation, the whitening booster may consist of the salt of the monopersulfate.

In at least one implementation, the whitening composition prior to use may be free or substantially free of water.

In at least one implementation, the orally acceptable vehicle may include a structure-building agent.

In at least one implementation, the structure-building agent may include an amphiphilic copolymer. The amphiphilic copolymer may include a polyvinylpyrrolidone vinyl acetate copolymer.

In at least one implementation, the structure-building agent may include a poloxamer. The poloxamer may include a poly(ethylene glycol)-block-poly(propylene glycol)-block-poly(ethylene glycol).

In at least one implementation, the source of hydrogen peroxide may include a cross-linked polyvinylpyrrolidone (PVP) hydrogen peroxide complex.

In at least one implementation, the oral care composition may be a tooth whitening gel.

In at least one implementation, the whitening booster may be present in an amount of from about 1 weight % to about 5 weight %, based on a total weight of the oral care composition.

The foregoing and/or other aspects and utilities embodied in the present disclosure may be achieved by providing a method for whitening teeth of a subject. The method may include contacting an oral care composition with a surface of the teeth of the subject in need thereof. The oral care composition may be any one or more of the oral care compositions disclosed herein. The oral care composition may include an orally acceptable vehicle, a whitening booster, and a source of hydrogen peroxide. The whitening booster may be dispersed in the orally acceptable vehicle, and may include a salt of a monopersulfate.

In at least one implementation, contacting the oral care composition with the surface of the teeth may include directly applying the oral care composition with a delivery device. The delivery device may be an applicator including a brush, a roller ball, or a felt tip.

In at least one implementation, contacting the oral care composition with the surface of the teeth may include disposing the oral care composition in a dental tray, and disposing the dental tray about the teeth.

In at least one implementation, the oral care composition may be contacted with the surface of the teeth for at least 5 minutes, optionally, at least 10 minutes, further optionally, at least 15 minutes.

Further areas of applicability of the present disclosure will become apparent from the detailed description provided hereinafter. It should be understood that the detailed description and specific examples, while indicating some typical aspects of the disclosure, are intended for purposes of illustration only and are not intended to limit the scope of the disclosure.

DETAILED DESCRIPTION

The following description of various typical aspect(s) is merely exemplary in nature and is in no way intended to limit the disclosure, its application, or uses.

As used throughout this disclosure, ranges are used as shorthand for describing each and every value that is within the range. It should be appreciated and understood that the description in a range format is merely for convenience and brevity, and should not be construed as an inflexible limitation on the scope of any embodiments or implementations disclosed herein. Accordingly, the disclosed range should be construed to have specifically disclosed all the possible subranges as well as individual numerical values within that range. As such, any value within the range may be selected as the terminus of the range. For example, description of a range such as from 1 to 5 should be considered to have specifically disclosed subranges such as from 1.5 to 3, from 1 to 4.5, from 2 to 5, from 3.1 to 5, etc., as well as individual numbers within that range, for example, 1, 2, 3, 3.2, 4, 5, etc. This applies regardless of the breadth of the range.

Unless otherwise specified, all percentages and amounts expressed herein and elsewhere in the specification should be understood to refer to percentages by weight. The amounts given are based on the active weight of the material.

Additionally, all numerical values are "about" or "approximately" the indicated value, and take into account experimental error and variations that would be expected by a person having ordinary skill in the art. It should be appreciated that all numerical values and ranges disclosed herein are approximate values and ranges, whether "about" is used in conjunction therewith. It should also be appreciated that the term "about," as used herein, in conjunction with a numeral refers to a value that may be ±0.01% (inclusive), ±0.1% (inclusive), ±0.5% (inclusive), ±1% (inclusive) of that numeral, ±2% (inclusive) of that numeral, ±3% (inclusive) of that numeral, ±5% (inclusive) of that numeral, ±10% (inclusive) of that numeral, or ±15% (inclusive) of that numeral. It should further be appreciated that when a numerical range is disclosed herein, any numerical value falling within the range is also specifically disclosed.

As used herein, "free" or "substantially free" of a material may refer to a composition, component, or phase where the material is present in an amount of less than 10.0 weight %, less than 5.0 weight %, less than 3.0 weight %, less than 1.0 weight %, less than 0.1 weight %, less than 0.05 weight %, less than 0.01 weight %, less than 0.005 weight %, or less than 0.0001 weight % based on a total weight of the composition, component, or phase.

All references cited herein are hereby incorporated by reference in their entireties. In the event of a conflict in a definition in the present disclosure and that of a cited reference, the present disclosure controls.

The present inventors have surprisingly and unexpectedly discovered that incorporating a whitening booster, such as monopersulfate (MPS) or a salt thereof, in an oral care product or the whitening composition thereof provided a surprising and unexpected increase in whitening efficacy as compared to a conventional oral care product (i.e., whitening gel) including hydrogen peroxide alone. The inventors have also surprisingly and unexpectedly discovered that the combination of MPS and hydrogen peroxide exhibits synergistic effects (e.g., more than additive) that provide a statistically significant enhancement or increase in whitening efficacy for oral care product or the whitening composition thereof. Particularly, oral care products or the whitening compositions thereof that combine MPS and hydrogen peroxide provide whiter teeth at a faster rate.

COMPOSITIONS

Compositions disclosed herein may be or include an oral care product, an oral care composition, and/or a whitening composition thereof. For example, the composition may be an oral care product or composition including a whitening composition, or the whitening composition thereof. In a typical implementation, the composition may be an oral care composition in the form of a gel. The whitening composition may include a carrier or an orally acceptable vehicle combined with one or more whitening agents, one or more sources of hydrogen peroxide, or combinations or mixtures thereof. For example, the whitening composition may include the one or more whitening boosters and the one or more sources of hydrogen peroxide, and the orally acceptable vehicle. In another example, the whitening composition may include the one or more whitening boosters and the orally acceptable vehicle. The one or more whitening boosters and/or the one or more sources of hydrogen peroxide may be combined with, dispersed in, mixed with, or otherwise contacted with the carrier or orally acceptable vehicle. The whitening booster may be or include one or more non-peroxide bleaching or whitening agents capable of or configured to interact synergistically with one or more components of the oral care product to enhance the whitening efficacy of the oral care product or the whitening composition thereof.

In at least one implementation, the oral care product or the whitening composition thereof may be anhydrous or non-aqueous prior to use. For example, the oral care product or the whitening composition thereof may be free of water, substantially free of water. As used herein, "free of water" or "substantially free of water" may refer to a composition that contains water in an amount of less than 10 weight %, less than 8 weight %, less than 5 weight %, less than 3 weight %, less than 1 weight %, less than 0.1 weight %, less than 0.05 weight %, less than 0.01 weight %, less than 0.005 weight %, or less than 0.0001 weight %, based on a total weight of the oral care product or the whitening composition thereof. In another implementation, the oral care product or the whitening composition thereof prior to use may have "low water content". As used herein, "low water content" may refer to a composition that contains water in an amount greater than about 5 weight % or greater than about 10 weight %, and less than about 20 weight %, less than about 15 weight %, or less than about 10 weight %, based on a total weight of the oral care product or the whitening composition thereof.

In one implementation, contacting the whitening composition or a component thereof with water may initiate the release of hydrogen peroxide. For example, contacting the source of hydrogen peroxide with water may initiate the release of hydrogen peroxide. In another example, the source of hydrogen peroxide may be maintained in a hydrophobic phase, and combining, mixing, or otherwise contacting the hydrophobic phase and a separate hydrophilic phase with one another may initiate the release of hydrogen peroxide from the source of hydrogen peroxide.

Sources of Hydrogen Peroxide

The one or more sources of hydrogen peroxide may be or include any compound or material capable of or configured to interact or react synergistically with the whitening booster to enhance or increase the whitening efficacy of the oral care product or the whitening composition thereof. For example, the one or more sources of hydrogen peroxide may be or include any compound or material capable of or configured to provide or release hydrogen peroxide that interacts or react synergistically with the whitening booster to enhance or increase the whitening efficacy of the oral care product or the whitening composition thereof. The sources of hydrogen peroxide may be capable of or configured to release hydrogen peroxide when contacted with water. Illustrative sources of hydrogen peroxide may be or include, but are not limited to, hydrogen peroxide, urea peroxide, calcium peroxide, a cross-linked polyvinylpyrrolidone (PVP) hydrogen peroxide complex, a polyvinylpyrrolidone (PVP) hydrogen peroxide complex, sodium percarbonate, or the like, or combinations thereof. The sources of hydrogen peroxide may also be or include, but are not limited to, PEROXYDONE™ XL 10F complex, which is commercially available from Ashland Inc. of Covington, Ky. In a typical implementation, the source of hydrogen peroxide includes a cross-linked polyvinylpyrrolidone (PVP) hydrogen peroxide complex.

The amount or concentration of the source of hydrogen peroxide may vary widely, and may depend upon the amount or a desired amount of hydrogen peroxide provided or otherwise delivered by the source of hydrogen peroxide. In at least one implementation, the source of hydrogen peroxide may be present in an amount that provides from greater than 0.0 weight % to less than or equal to 35.0 weight % free hydrogen peroxide, based on a total weight of the oral care product or the whitening composition thereof. For example, the source of hydrogen peroxide may be present in an amount that provides hydrogen peroxide (e.g., free hydrogen peroxide) in an amount of from greater than 0.0 weight %, about 0.5 weight %, about 1.0 weight %, about 1.5 weight %, about 2.0 weight %, about 2.5 weight %, about 3.0 weight %, about 3.5 weight %, about 4.0 weight %, about 4.5 weight %, about 5.5 weight %, about 6.0 weight %, about 6.5 weight %, about 7.0 weight %, about 7.5 weight %, about 8.0 weight %, about 8.5 weight %, about 9.0 weight %, about 9.5 weight %, or about 10.0 weight % to about 12.0 weight %, about 14.0 weight %, about 16.0 weight %, about 18.0 weight %, about 20.0 weight %, about 22.0 weight %, about 24.0 weight %, about 26.0 weight %, about 28.0 weight %, about 30.0 weight %, about 32.0 weight %, about 34.0 weight %, or less than or equal to about 35.0 weight %, based on a total weight of the oral care product or the whitening composition thereof.

In another implementation, the source of hydrogen peroxide may be present in an amount that provides from greater than 0.0 weight % to less than or equal to 10.0 weight % free hydrogen peroxide, based on a total weight of the oral care product or the whitening composition thereof. For example, the source of hydrogen peroxide may be present in an amount that provides hydrogen peroxide (e.g., free hydrogen peroxide) in an amount of from greater than 0.0 weight %, about 0.5 weight %, about 1.0 weight %, about 1.5 weight %, about 2.0 weight %, about 2.5 weight %, about 3.0 weight %, about 3.5 weight %, about 4.0 weight %, or about 4.5 weight % to about 5.5 weight %, about 6.0 weight %, about 6.5 weight %, about 7.0 weight %, about 7.5 weight %, about 8.0 weight %, about 8.5 weight %, about 9.0 weight %, about 9.5 weight %, or about 10.0 weight %, based on a total weight of the oral care product or the whitening composition thereof. In another example, the source of hydrogen peroxide may be present in an amount that provides hydrogen peroxide in an amount of from greater than 0.0 weight % to less than or equal to 10.0 weight %, about 0.5 weight % to about 9.5 weight %, about 1.0 weight % to about 9.0 weight %, about 1.5 weight % to about 8.5 weight %, about 2.0 weight % to about 8.0 weight %, about 2.5 weight % to about 7.5 weight %, about 3.0 weight % to about 7.0 weight %, about 3.5 weight % to about 6.5 weight %, about 4.0 weight % to about 6.0 weight %, or about 4.5 weight % to about 5.5 weight %.

In yet another implementation, the source of hydrogen peroxide may be present in an amount that provides from about 0.1 weight % to less than or equal to 2.0 weight % free hydrogen peroxide, based on a total weight of the oral care product or the whitening composition thereof. For example, the source of hydrogen peroxide may be present in an amount that provides hydrogen peroxide (e.g., free hydrogen peroxide) in an amount of from about 0.1 weight %, about 0.2 weight %, about 0.3 weight %, about 0.4 weight %, about 0.5 weight %, about 0.6 weight %, about 0.7 weight %, about 0.8 weight %, about 0.9 weight %, or about 1.0 weight % to about 1.1 weight %, about 1.2 weight %, about 1.3 weight %, about 1.4 weight %, about 1.5 weight %, about 1.6 weight %, about 1.7 weight %, about 1.8 weight %, about 1.9 weight %, or about 2.0 weight %. In another example, the source of hydrogen peroxide may be present in an amount that provides hydrogen peroxide in an amount of from about 0.1 weight % to about 2.0 weight %, about 0.2 weight % to about 1.9 weight %, about 0.3 weight % to about 1.8 weight %, about 0.4 weight % to about 1.7 weight %, about 0.5 weight % to about 1.6 weight %, about 0.6 weight % to about 1.5 weight %, about 0.7 weight % to about 1.4 weight %, about 0.8 weight % to about 1.3 weight %, about 0.9 weight % to about 1.2 weight %, or about 1.0 weight % to about 1.1 weight %. In yet another example, the source of hydrogen peroxide may be present in an amount that provides hydrogen peroxide in an amount less than or equal to 2.0 weight %, less than or equal to 1.8 weight %, less than or equal to 1.6 weight %, less than or equal to 1.4 weight %, less than or equal to 1.2 weight %, less than or equal to 1.0 weight %, less than or equal to 0.8 weight %, less than or equal to 0.6 weight %, or less than or equal to 0.4 weight %. In a typical implementation, the source of hydrogen peroxide may be present in an amount that provides hydrogen peroxide in an amount of about 35.0 weight % or less, or about 2.5 weight % or less, or about 2.0 weight % or less.

Whitening Booster

The whitening booster may be or include any compound or material capable of or configured to interact or react synergistically with the source of hydrogen peroxide or the hydrogen peroxide thereof to enhance the whitening efficacy of the oral care product or the whitening composition thereof. In at least one implementation, the whitening booster may be or include one or more non-peroxide bleaching or whitening agents. The whitening booster or the non-peroxide bleaching agent may be water soluble. Illustrative non-peroxide bleaching agents may be or include, but are not limited to, a salt of a peroxymonosulfate or a salt of monopersulfate (MPS). For example, the whitening booster may be or include, but is not limited to, an alkali metal salt of MPS, such as a potassium MPS, sodium MPS, ammonium MPS, or the like, or any combination thereof. MPS may be provided as a single molecule, a compound, such as a monopersulfate compound or MPS compound, a complex, such as a monopersulfate complex, or any combination thereof. In at least one implementation, the whitening booster may be or include an MPS compound or a mixture of two or more salts of peroxymonosulfate. The MPS compound may be or include a mixed salt or triple salt, such as $(2KHSO_5 \cdot KHSO_4 \cdot K_2SO_4)$.

In at least one implementation, the whitening booster may be or include OXONE®, which is commercially available from DuPont of Wilmington, Del. It should be appreciated that OXONE® has an active oxygen content of about 4.5%. The active oxygen content of the mixed salt is about 5.2% when the salt is purified. The active oxygen content of $KHSO_5$ is about 10.5%. It should further be appreciated that the pure mixed salt has about half as much active oxygen as compared to the pure form, and the 86.5% pure mixed salt (i.e., OXONE®) has 43% as much active oxygen as compared to the pure form. It should also be appreciated that OXONE® may include about 43% potassium hydrogen peroxymonosulfate, about 23% potassium hydrogen sulfate, about 29% potassium sulfate, about 3% potassium peroxydisulfate, and about 2% magnesium carbonate. MPS is also commercially available as CAROAT® from United Initiators Inc. of Mason, Ohio.

In at least one implementation, the whitening booster may be provided as a solid. For example, the whitening booster may be provided as a powder, a tablet, granules, or the like, and the whitening booster may be combined with the remaining components to form the oral care product (e.g., gel) or the whitening composition thereof. It should be appreciated that the solid may be free or substantially free of water. The solid may be provided in a variety of forms, including, but not limited to, a free flowing granulation, a tablet (e.g., effervescing tablet), a caplet, granules, pellets, wafers, films, beads, or the like. In another implementation, the whitening booster may be provided as a liquid, mixture, or solution, such as a liquid dispersion of the solid.

The whitening booster may be provided separate from one or more of the remaining components or ingredients of the whitening composition, and at the point of use, the whitening booster may be combined, mixed, dispersed, or otherwise contacted with the one or more remaining components to form the oral care product or the whitening composition thereof. For example, the whitening booster may be provided as a solid and contacted with the one or more remaining components to form or provide the oral care product or the whitening composition thereof.

In at least one implementation, the whitening booster may be provided in an air-tight, moisture-proof container, package, vessel, or the like. Illustrative packages may be or include, but are not limited to, sealed metal foil pouches, blister packs, desiccant capped tubes, or the like. The packages may be made from polymeric materials, such as polyethylene, polypropylene, or the like or copolymers thereof, metallic materials, such as metallic foils (e.g., aluminum), or both the polymeric and metallic materials. The whitening booster may be packaged as a single dose or multiple doses.

The amount or concentration of the whitening booster may vary widely. In at least one implementation, the whitening booster may be provided in an amount of from greater than 0.0 weight % to about 30 weight %, based on a total weight of the oral care product or the whitening composition thereof. For example, the whitening booster may be provided in an amount from greater than 0.0 weight %, about 0.5 weight %, about 1 weight %, about 1.5 weight %, about 2 weight %, about 2.5 weight %, about 3 weight %, about 3.5 weight %, about 4 weight %, or about 4.5 weight % to about 5 weight %, about 5.5 weight %, about 6 weight %, about 6.5 weight %, about 7 weight %, about 7.5 weight %, about 8 weight %, about 8.5 weight %, about 9 weight %, about 9.5 weight %, about 10 weight %, about 15 weight %, about 20 weight %, about 25 weight %, or about 30 weight %. In another example, the whitening booster may be provided in an amount from greater than 0.0 weight %, about 0.1 weight %, about 0.2 weight %, about 0.3 weight %, about 0.4 weight %, about 0.5 weight %, about 0.6 weight %, about 0.7 weight %, about 0.8 weight %, about 0.9 weight %, or about 1.0 weight % to about 1.1 weight %, about 1.2 weight %, about 1.3 weight %, about 1.4 weight %, about 1.5 weight %, about 1.6 weight %, about 1.7 weight %, about 1.8 weight %, about 1.9 weight %, or about 2.0 weight %. In yet another example, the whitening booster may be provided in an amount from greater than 0.0 weight % to about 2.0 weight %, about 0.1 weight % to about 1.9 weight %, about 0.2 weight % to about 1.8 weight %, about 0.3 weight % to about 1.7 weight %, about 0.4 weight % to about 1.6 weight %, about 0.5 weight % to about 1.5 weight %, about 0.6 weight % to about 1.4 weight %, about 0.7 weight % to about 1.3 weight %, about 0.8 weight % to about 1.2 weight %, or about 0.9 weight % to about 1.1 weight %.

In at least one implementation, the amount of the whitening booster present in the whitening composition may be at least partially determined by or depend upon the amount of hydrogen peroxide provided or otherwise delivered by the source of hydrogen peroxide. For example, the whitening booster may be provided in an amount such that a ratio of the whitening booster to the amount of hydrogen peroxide provide by the source of hydrogen peroxide or vice versa may be from about 0.1:1 to about 5:1, or from about 0.1:1 to about 10:1, or from about 0.1:1 to about 15:1. For example, the ratio of the whitening booster to the amount of hydrogen peroxide provide by the source of hydrogen peroxide or vice versa may be from about 0.01:1, about 0.1:1, about 0.5:1, about 1:1, about 1.5:1, or about 2:1 to about 2.5:1, about 3:1, about 3.5:1, about 4:1, about 4.5:1, about 5:1, about 10:1, or about 15:1. In another example, the ratio of the whitening booster to the amount of hydrogen peroxide provide by the source of hydrogen peroxide or vice versa may be from about 0.1:1 to about 5:1, about 0.5:1 to about 4.5:1, about 1:1 to about 4:1, about 1.5:1 to about 3.5:1, or about 2:1 to about 3:1.

Orally Acceptable Vehicle Or Liquid Carrier

The whitening composition may form at least a portion of or be used in one or more oral care products or oral care compositions. The whitening composition may be mixed, dispersed, dissolved, combined, or otherwise contacted with an orally acceptable vehicle or carrier to form the oral care product (e.g., whitening gel) or oral care compositions. Illustrative oral care products may include, but are not limited to, a mouthwash, a toothpaste (dentifrice), a prophylactic paste, a tooth powder, a tooth polish, a tooth gel (e.g., a whitening gel), a chewing gum, a lozenge, a whitening strip, a paint-on gel, varnish, veneer, tube, syringe, dental tray including a gel or paste, a gel or paste coated on an application support such as dental floss or a toothbrush (e.g., a manual, electric, sound, a combination thereof or ultrasound toothbrush), or any combination thereof. In a typical implementation, the whitening composition may form at least a portion of or be used in a whitening gel or a gel whitening composition.

The orally acceptable vehicle may include one or more poloxamers. The poloxamers may be a liquid or a paste. The poloxamer may have an average molecular weight of less than or equal to about 12,000 Dalton (Da), less than or equal to about 11,000 Da, less than or equal to about 10,000 Da, less than or equal to about 9,000 Da, less than or equal to about 8,000 Da, less than or equal to about 7,000 Da, or less than or equal to about 6,000 Da. Illustrative poloxamers may be or include, but are not limited to, one or more of PLURONIC® L35 (poly(ethylene glycol)-block-poly(propylene glycol)-block-poly(ethylene glycol)), PLURONIC® L43, PLURONIC® L64, PLURONIC® L10, PLURONIC® L44, PLURONIC® L62, PLURONIC® 10R5, PLURONIC® 17R4, PLURONIC® L25R4, PLURONIC® P84, PLURONIC® P65, PLURONIC® P104, and PLURONIC® P105, or the like, or any mixture or combination thereof, each of which or commercially available from BASF Corp. of Florham Park, N.J. In a preferred implementation, the orally acceptable vehicle includes a poly(ethylene glycol)-block-poly(propylene glycol)-block-poly(ethylene glycol) polymer, such as PLURONIC® L35.

The orally acceptable vehicle may include a thickening system having one or more thickeners. The one or more thickeners may be any orally acceptable thickener or thickening agent configured to control the viscosity of the oral care product or the whitening composition thereof. Illustrative thickeners may be or include, but are not limited to, colloidal silica, fumed silica, polyvinylpyrrolidone (PVP), a cross-linked polyvinylpyrrolidone (PVP) polymer, cross-linked polyvinylpyrrolidone (PVP), or the like, or mixtures or combinations thereof. In at least one implementation, the thickening system includes a polyvinylpyrrolidone (PVP), cross-linked polyvinylpyrrolidone (PVP) polymer, or combinations thereof. The thickening system may also include POLYPLASDONE® XL 10F, which is commercially available from Ashland Inc. of Covington, Ky. Illustrative thickeners may also be or include, but are not limited to, carbomers (e.g., carboxyvinyl polymers), carrageenans (e.g., Irish moss, carrageenan, iota-carrageenan, etc.), high molecular weight polyethylene glycols (e.g., CARBOWAX®, which is commercially available from The Dow Chemical Company of Midland, Mich.), cellulosic polymers, hydroxyethylcellulose, carboxymethylcellulose, and salts thereof (e.g., CMC sodium), natural gums (e.g., karaya, xanthan, gum arabic, and tragacanth), colloidal magnesium aluminum silicate, or the like, or mixtures or combinations thereof.

In a more typical implementation, the thickening system may include an organic polymer, which may also be configured as an adhesion enhancing agent. Illustrative organic polymers may be or include, but are not limited to, hydrophilic polymers, such as carbomers, such as carboxymethylene polymers, such as acrylic acid polymers, and acrylic acid copolymers. carboxypolymethylene is a slightly acidic vinyl polymer with active carboxyl groups. In a typical embodiment, the thickening system includes a carboxypolymethylene, such as CARBOPOL® 974 and/or 980, which are commercially available from Noveon, Inc. of Cleveland, Ohio.

The amount or concentration of the thickening system and/or any one or more of the thickeners thereof present in the oral care product or the whitening composition thereof may vary widely. The amount of the thickening system and/or the thickeners thereof present in the oral care product or the whitening composition thereof may be from about 1 weight % to about 99 weight % based on the total weight of the oral care product or the whitening composition thereof. For example, the amount of the thickening system and/or the thickeners thereof present may be from about 1 weight %, about 2 weight %, about 3 weight %, about 4 weight %, about 5 weight %, about 6 weight %, about 7 weight %, about 8 weight %, about 9 weight %, about 10 weigh %, about 15 weight %, about 20 weight %, or about 21 weight % to about 22 weight %, about 23 weight %, about 24 weight %, about 25 weight %, about 26 weight %, about 27 weight %, about 28 weight %, about 29 weight %, about 30 weight %, or more, based on a total weight of the oral care product or the whitening composition thereof. In another example, the amount of the thickening system and/or the thickeners thereof present may be from about 1 weight % to about 30 weight %, about 3 weight % to about 29 weight %, about 14 weight % to about 28 weight %, about 15 weight % to about 27 weight %, about 16 weight % to about 26 weight %, about 17 weight % to about 25 weight %, about 18 weight % to about 24 weight %, about 19 weight % to about 23 weight %, or about 20 weight % to about 22 weight %. In a typical implementation, the amount of the thickening system and/or the thickeners thereof present in the oral care product or the whitening composition thereof may be from about 10 weight % to about 20 weight %, more typically about 1.2 weight % to about 1.8 weight %, and more typically about 1.5 weight %.

The orally acceptable vehicle may include one or more structure-building agents. As used herein, the term or expression "structure-building agent" may refer to a material that may not only thicken the oral care product or the whitening composition thereof, but may also maintain the oral care composition in a homogenous state. As used herein, the term or expression "homogenous" may refer to a mixture, solution, or composition composed of or including two or more compounds, elements, substances, or the like, that are uniformly dispersed into one another. A homogenous oral care composition may be capable of maintaining or exhibiting no phase separation after aging for at least 12 hours, at least 24 hours, at least 36 hours, at least 2 days, at least 3 days, at least 5 days, at least 10 days, at least 15 days, at least 20 days, at least 30 days, at least 2 months, at least 3 months, at least 5 months, at least 6 months, or at least 1 year.

Without being bound by the theory, it is believed that structure-building agents may generally interact with the one or more components of the orally acceptable vehicle and/or other structure building agents to maintain the homogenous state. For example, the structure-building agent may be capable of or configured to form a gel or a gel structure via self-assembly. The structure-building agent may be capable of or configured to form a gel with the other structure-building agents and/or the one or more components of the orally acceptable vehicle by interacting with the other structure-building agents and/or the one or more components of the orally acceptable vehicle via any one or more intermolecular forces (e.g., van der Waal, dipole-dipole, hydrogen bonding, covalent bonding, etc.).

In some implementations, the structure-building agent may be or include a polymer. In some examples, the structure-building agent may be or include an amphiphilic copolymer, where the amphiphilic copolymer is composed of two or more monomers, where at least one of the monomers is hydrophilic (e.g., vinylpyrrolidone), and where at least one of the monomers is hydrophobic (e.g., vinyl acetate). It should be appreciated that an amphiphilic copolymer may be capable of or configured to interact with both hydrophilic and hydrophobic components, substances, or liquids. In at least one implementation, the structure-building agent may be or include, but is not limited to, a poloxamer, as described above, a cross-linked polymer, such as cross-linked polyvinylpyrrolidone ("PVP"), a polyvinylpyrrolidone copolymer, a polyvinylpyrrolidone vinyl acetate copolymer, or any combination thereof. It should be appreciated that the cross-linked PVP swells in the presence of L35 by absorbing L35 into its cross-linked polymer network. The interaction between a cross-linked PVP and L35 may facilitate to formation of a homogenous gel by preventing a solid cross-linked PVP from phase separating from a liquid L35.

Illustrative structure-building agent agents may be or include, but are not limited to, N-vinyl lactam based polymers and copolymers. The monomers for preparing a vinyl lactam-based polymer or co-polymer of the present application includes any monomer having 3 to 8 atoms in a heterocyclic ring, comprising a carbonyl carbon atom and a heteroatom (such as N, S, O) in its vinyl moiety. Suitable monomers include but not limited to N-vinyl-2-pyrrolidone, N-vinyl-2-piperidone, N-vinyl-3-methyl-pyrrolidinone, N-vinyl-3-methyl-piperidone, N-vinyl-3-methyl-caprolactam, N-vinyl-4-methyl-pyrrolidinone, N-vinyl-4-methyl-2-pyrrolidone, N-vinyl-4-methyl-piperidone, N-vinyl-4-methyl-caprolactam, N-vinyl-5-methyl-pyrrolidinone, N-vinyl-5-ethyl-2-pyrrolidone, N-vinyl-4-methyl-piperidone, N-vinyl-3-ethyl-pyrrolidinone, N-vinyl-4,5-dimethyl-pyrrolidinone, N-vinyl-5,5-dimethyl-pyrrolidinone, N-vinyl-3,3,5-trimethyl-pyrrolidinone, N-vinyl-5-methyl-5-ethyl-pyrrolidinone, N-vinyl-3,4,5-trimethyl-3-ethyl-pyrrolidinone, N-vinyl-6-methyl-2-piperidone, N-vinyl-6-ethyl-2-piperidone, N-vinyl-3,5-dimethyl-2-piperidone, N-vinyl-4,4-dimethyl-2-piperidone, N-vinyl-2-caprolactam, N-vinyl-7-methyl-caprolactam, N-vinyl-7-ethyl-caprolactam, N-vinyl-3,5-dimethyl-caprolactam, N-vinyl-4,6-dimethyl-caprolactam, N-vinyl-3,5,7-trimethyl-caprolactam, N-vinyl-2-valerolactam, N-vinyl-hexahydro-2-azepinone, N-vinyl-octahydro-2-azocinone, N-vinyl octahydro-2-azoninone, N-vinyl decahydro-2-azecinone, or the like, or combinations thereof.

The amount or concentration of any one or more of the structure-building agents present in the oral care product or the whitening composition thereof may vary widely. The amount of any one or more of the structure-building agents present in the oral care product or the whitening composition thereof may be from about 1 weight % to about 99 weight %, based on the total weight of the oral care product or the whitening composition thereof. For example, the amount of the thickening system and/or the thickeners thereof present may be from about 1 weight %, about 2 weight %, about 3 weight %, about 4 weight %, about 5 weight %, about 6 weight %, about 7 weight %, about 8 weight %, about 9 weight %, about 10 weigh %, about 15 weight %, about 20 weight %, or about 21 weight % to about 22 weight %, about 23 weight %, about 24 weight %, about 25 weight %, about 26 weight %, about 27 weight %, about 28 weight %, about 29 weight %, about 30 weight %, or more, based on a total weight of the oral care product or the whitening composition thereof. In another example, the amount of any one or more of the structure-building agents present may be from about 1 weight % to about 99 weight %, about 3 weight % to about 90 weight %, about 14 weight % to about 80 weight %, about 15 weight % to about 80 weight %, about 16 weight % to about 70 weight %, about 17 weight % to about 60 weight %, about 18 weight % to about 50 weight %, about 19 weight % to about 40 weight %, or about 20 weight % to about 30 weight %. In a typical implementation, the amount of any one or more of the structure-building agents present in the oral care product or the whitening composition thereof may be from about 10 weight % to about 20 weight %, more typically about 1.2 weight % to about 1.8 weight %, and more typically about 1.5 weight %.

In some implementations, the oral care product or the orally acceptable vehicle thereof may include a hydrophobic component or base material. The hydrophobic component may be or include a hydrophobic polymer, such as a silicone polymer. The term "hydrophobic" or "water-insoluble" as applied to polymers and as employed herein may refers to an organic polymer that is substantially non-aqueous and having a water solubility of less than one gram per 100 grams of water at 25° C. Any such silicone polymers that are compatible with the components disclosed herein, and that can produce the oral care product or the whitening composition thereof having a desired viscosity may be used.

In some implementations, the hydrophobic polymers suitable for use in the present invention may be referred to as "siloxane" polymers, which are also generally known in the art as "silicone" polymers. In certain implementations, the hydrophobic polymers may include those in which a whitening agent may be dispersed. In a preferred implementation, the hydrophobic polymers may be or include, but are not limited to, silicone-based hydrophobic polymer, such as polyorganosiloxane, in particular polydimethylsiloxane.

In some implementations, the siloxane polymers that may function as part of the hydrophobic component are in the form of a fluid. Polysiloxane fluids useful herein for the hydrophobic silicone material component include those with a viscosity, as measured at 25° C., of about 1 centipoise (cP) to about 1000 cP, or about 2 cP to about 500 cP, or about 20 cP to about 400 cP. Polysiloxane fluids for use herein may be linear or cyclic, and may be substituted with a wide variety of substituents. The substituents may be or include, but are not limited to, methyl, ethyl, phenyl substituents, or the like, or mixtures thereof. Suitable polysiloxane fluids may include linear polysiloxane polymers such as dimethicone and other low viscosity analogues of the polysiloxane materials, having a viscosity of about 200 cP or less and cyclomethicone, and other cyclic siloxanes having a viscosity of about 200 cP or less. Other fluids include polysiloxane polyether copolymers and hydroxy terminated polydimethyl-siloxane fluid (e.g., Dow Corning ST-DIMETHICONOL.™ 40, Dow Corning SGM 36, SGM3). Commercial examples of materials that are suitable for use herein include DC200 series fluids marketed by Dow-Corning Corporation and the AK Fluid series marketed by Wacker-Chemie GmbH, Munchen, Germany. High molecular silicone resins with a polysiloxane blend may also be used including powdered trimethylsiloxysilicate, for example, Dow Corning 593 fluid, Wacker Belsil TMS 803. Another suitable silicone fluid from Dow Corning is Q7-9210.

In some implementations, the hydrophobic component may be or include a silicone fluid. In some implementations, the silicone fluid may be or include a siloxane polymer.

The hydrophobic component may be present in the oral care product or the whitening composition thereof in an amount of from about 10 weight % to about 95 weight %, about 10 weight % to about 80 weight %, about 10 weight % to about 60 weight %, about 10 weight % to about 40 weight %, about 10 weight % to about 30 weight %, based on a total weight of the oral care product or the whitening composition thereof.

Adhesive or Adhesion Enhancing Agent

In at least one implementation, the oral care product or the whitening composition thereof may optionally include one or more adhesives configured to improve, maintain, and/or facilitate the adhesion of the oral care product or the whitening composition thereof to surfaces of the oral cavity. The one or more adhesives may also be configured to increase the hydrophobicity of a film formed from the oral care product or the whitening composition thereof, thereby allowing the film to withstand external challenges, such as abrading, rubbing, or brushing.

Illustrative adhesives may be or include, but are not limited to, alkyd resins, polyvinyl acetaldehydes, polyvinyl alcohols, polyvinyl acetates, poly(ethylene oxide), polyacrylates, ketone resins, polyvinylpyrolidone, polyvinylpyrolidone/vinyl acetate copolymer, polyethylene glycols of 200 to 1000 molecular weight, polyoxyethylene/polyoxopropylene block copolymers (Polyox), silicon resins, or the like, and mixtures or combinations thereof. In at least one implementation, the one or more adhesives may include siloxane polymers, which are also generally known in the art as "silicone" polymers. Illustrative silicone-based hydrophobic polymers may be or include, but are not limited to, polyorganosiloxane, polydiorganosiloxane, and the like, and combinations thereof. In at least one implementation, the adhesion enhancing agent includes at least one silicon pressure sensitive adhesive (PSA). Such PSAs may be pressure sensitive hydrophobic polymers specifically designed for pharmaceutical use and are permeable to many drug compounds and find application for the transdermal application of various compounds. In some implementations, the silicone polymers are the copolymer product of mixing a silanol terminated polydiorganosiloxane, such as polydimethyl siloxane, with a silanol-containing silicone resin, whereby the silanol groups of the polydiorganosiloxane undergo a condensation reaction with the silanol groups of the silicone resin such that the polydiorganosiloxane is lightly cross-linked by the silicone resin (that is, the polydiorganosiloxane chains are bonded together through the resin molecules to give chain branching and entanglement and/or a small amount of network character) to form the silicone hydrophobic polymers. In at least one implementation, the adhesion enhancing agents are available under the trade name BIO-PSA from the Dow Corning Company of Midland, Mich. The modification of a ratio of silicone resin to polydiorganosiloxane modifies the tackiness of the polymer. This ratio may be in the range of about 70:30 to about 50:50. For example, the BIO-PSA silicone commercially available from Dow-Corning is available in varying silicone resin to silicone polymer ratios, namely, 65/35 (low tack), 60/40 (medium tack), and 55/45 (high tack). Such a polyorganosiloxane PSA is available dissolved in either ethyl acetate solvent or dimethicone. In at least one implementation, the adhesion enhancing agent may include Silicone Adhesive 8-7016, commercially available from Dow Corning Corporation of Midland, Mich.

The one or more adhesives or adhesion enhancing agents may be present in the oral care product or the whitening composition thereof in an amount of from about 10 weight % to about 80 weight %, about 10 weight % to about 60 weight %, about 10 weight % to about 50 weight %, about 10 weight % to about 40 weight %, about 10 weight % to about 30 weight %, based on a total weight of the oral care product or the whitening composition thereof.

Flavoring Agents

The oral care product or the whitening composition thereof may also include one or more flavoring agents. Illustrative flavoring agents may include, but are not limited to, essential oils and various flavoring aldehydes, esters, alcohols, or the like. The flavoring agents may also include, but are not limited to, sweeteners, sucralose, dextrose, polydextrose, sucrose, maltose, dextrin, dried invert sugar, mannose, xylose, ribose, fructose, levulose, galactose, corn syrup (including high fructose corn syrup and corn syrup solids), partially hydrolyzed starch, hydrogenated starch hydrolysate, sorbitol, mannitol, xylitol, maltitol, isomalt, aspartame, neotame, saccharin and salts thereof (e.g., sodium saccharin), dipeptide-based intense sweeteners, cyclamates, dihydrochalcones, or the like, or mixtures thereof. Examples of the essential oils include oils of spearmint, peppermint, wintergreen, sassafras, clove, sage, eucalyptus, marjoram, cinnamon, lemon, lime, grapefruit, and orange. In another example, the flavoring agents may include menthol, carvone, and anethole. In a preferred implementation, the flavoring agent includes peppermint and spearmint. In a more preferred implementation, the flavoring agent includes a Firmenich Newman Flavor.

The amount of any one or more of the flavoring agent in the oral care product or the whitening composition thereof may be less than 1.0 weight %, less than 0.9 weight %, less than 0.8 weight %, or less than 0.7 weight %. For example, the amount of the flavoring agent in the oral care product or the whitening composition thereof may be about 0.0 weight % to about 1.0 weight %, about 0.5 weight % to about 0.9 weight %, about 0.7 weight % to about 0.8 weight %. In a preferred implementation, the amount of the flavoring agent in the oral care product or the whitening composition thereof is about 0.01 weight % to about 0.4 weight %, preferably about 0.1 weight % to about 0.3 weight %, or about 0.2 weight %.

Additional Ingredients

It should be appreciated to one having ordinary skill in the art, that the oral care products and/or the whitening composition thereof may include other additional ingredients/components. For example, the oral care products and/or the whitening composition thereof may include anti-caries agents, desensitizing agents, viscosity modifiers, diluents, mouth feel agents, colorants, preservatives, or the like, or combinations or mixtures thereof. It should further be appreciated by one having ordinary skill in the art that while general attributes of each of the above categories of materials may differ, there may be some common attributes and any given material may serve multiple purposes within two or more of such categories of materials.

In at least one implementation, the additional ingredients/components may include one or more active materials configured to prevent and/or treat one or more conditions and/or disorders of the oral cavity. For example, the one or more active materials may be configured to prevent and/or treat one or more conditions and/or disorders of hard and/or soft tissue of the oral cavity. The active materials may also be configured to prevent and/or treat one or more physiological disorders and/or conditions, and/or provide a cosmetic benefit to the oral cavity.

In at least one implementation, the oral care products and/or the whitening composition thereof may include an anticalculus agent. Generally, anticalculus agents may not be compatible with some whitening compositions, however, implementations of the present disclosure may incorporate anticalculus agents and the whitening composition into a single phase oral care product. Illustrative anticalculus agents may include, but are not limited to, phosphates and polyphosphates (e.g., pyrophosphates), polyaminopropanesulfonic acid (AMPS), hexametaphosphate salts, zinc citrate trihydrate, polypeptides, polyolefin sulfonates, polyolefin phosphates, diphosphonates. In a typical implementation, the anticalculus agents includes tetrasodium pyrophosphate (TSPP), sodium tripolyphosphate (STPP), or a combination thereof.

The oral care products and/or the whitening composition thereof may optionally include one or more antimicrobial agents and/or one or more preservatives such as, methylisothiazolinone (MIT), sodium benzoate, potassium sorbate, benzyl alcohol, or the like, or combinations thereof. In another example, the oral care composition may include one or more antibacterial agents selected from halogenated diphenyl ether (e.g. triclosan), herbal extracts and essential oils (e.g., rosemary extract, tea extract, magnolia extract, thymol, menthol, eucalyptol, geraniol, carvacrol, citral, hinokitol, catechol, methyl salicylate, epigallocatechin gallate, epigallocatechin, gallic acid, miswak extract, sea-buckthorn extract), bisguanide antiseptics (e.g., chlorhexidine, alexidine or octenidine), quaternary ammonium compounds (e.g., cetylpyridinium chloride (CPC), benzalkonium chloride, tetradecylpyridinium chloride (TPC), N-tetradecyl-4-ethylpyridinium chloride (TDEPC)), phenolic antiseptics, hexetidine, octenidine, sanguinarine, povidone iodine, delmopinol, salifluor, other metal ions (e.g., stannous salts, copper salts, iron salts), sanguinarine, propolis and oxygenating agents (e.g., hydrogen peroxide, buffered sodium peroxyborate or peroxycarbonate), phthalic acid and its salts, monoperthalic acid and its salts and esters, ascorbyl stearate, oleoyl sarcosine, alkyl sulfate, dioctyl sulfosuccinate, salicylanilide, domiphen bromide, delmopinol, octapinol, and other piperidino derivatives, nicin preparations, chlorite salts; or mixtures of any of the foregoing. In a typical implementation, the antibacterial agent includes cetylpyridinium chloride (CPC). For example, all of the dual-phase mouthwash compositions disclosed herein may include CPC as an antibacterial agent.

The oral care products and/or the whitening composition thereof may include an antioxidant. Any orally acceptable antioxidant may be used, including, but not limited to, butylated hydroxyanisole (BHA), butylated hydroxytoluene (BHT), vitamin A, carotenoids, vitamin E, flavonoids, polyphenols, ascorbic acid, herbal antioxidants, chlorophyll, melatonin, or the like, or combinations or mixtures thereof.

The amount or concentration of any one or more of the additional ingredients/components present in the oral care product or the whitening composition thereof may vary widely. The amount of any one or more of any one or more of the additional ingredients/components present in the oral care product or the whitening composition thereof may be from about 1 weight % to about 99 weight %, based on the total weight of the oral care product or the whitening composition thereof. For example, the amount of any one or more of the additional ingredients/components present may be from about 1 weight %, about 2 weight %, about 3 weight %, about 4 weight %, about 5 weight %, about 6 weight %, about 7 weight %, about 8 weight %, about 9 weight %, about 10 weigh %, about 15 weight %, about 20 weight %, or about 21 weight % to about 22 weight %, about 23 weight %, about 24 weight %, about 25 weight %, about 26 weight %, about 27 weight %, about 28 weight %, about 29 weight %, about 30 weight %, or more, based on a total weight of the oral care product or the whitening composition thereof. In another example, the amount of any one or more of the additional ingredients/components present may be from about 1 weight % to about 99 weight %, about 3 weight % to about 90 weight %, about 14 weight % to about 80 weight %, about 15 weight % to about 80 weight %, about 16 weight % to about 70 weight %, about 17 weight % to about 60 weight %, about 18 weight % to about 50 weight %, about 19 weight % to about 40 weight %, or about 20 weight % to about 30 weight %. In a typical implementation, the amount of any one or more of the additional ingredients/components present in the oral care product or the whitening composition thereof may be from about 10 weight % to about 20 weight %, more typically about 1.2 weight % to about 1.8 weight %, and more typically about 1.5 weight %.

All ingredients for use in the compositions described herein should be orally acceptable. By "orally acceptable" as the term is used herein is meant an ingredient that is present in a composition as described in an amount and form that does not render the composition unsafe for use in the oral cavity.

METHODS

The present disclosure also provides methods for whitening teeth in a human or animal subject with the oral care product and/or the whitening composition disclosed herein. As used herein "animal subject" may include higher order non-human mammals such as canines, felines, and horses. The method may include contacting the oral care product, the whitening composition, or the source of hydrogen peroxide thereof with water to initiate the formation of hydrogen peroxide. The method may also include contacting the oral care product or the whitening composition thereof with surfaces of the oral cavity, such as surfaces of teeth.

In some implementations, contacting the surface of the teeth with the oral care product or the whitening composition thereof may include directly applying the oral care product or the whitening composition to the teeth using a delivery device, such as a pen, (e.g., a COLGATE® whitening pen or a COLGATE® ACTIST™ whitening pen, Colgate--Palmolive Company, New York, N.Y.), a liquid stick having an applicator, such as a felt tip, brush, roller ball, non-woven pad, or the like. In another implementation, contacting the surface of the teeth with the oral care product or the whitening composition thereof may include disposing the oral care product or the whitening composition thereof in a dental tray (e.g., reservoir of the dental tray) and disposing the dental tray about the teeth. The oral care product or the whitening composition may be applied to the teeth and left for at least 2 minutes, at least 5 minutes, typically at least 10 minutes, or more typically at least 30 minutes. After each treatment with the tooth whitening composition the teeth may be treated with a tooth desensitizing formulation. Illustrative desensitizing formulations may contain potassium nitrate, citric acid, citric acid salts, strontium chloride or the like.

The oral care product and/or the whitening composition thereof may be applied and/or contacted with the surfaces of the teeth at predetermined intervals. For example, a daily basis, at least once a day for multiple days, or alternatively every other day. In another example, the oral care product and/or the whitening composition thereof may be applied and/or contacted with the surfaces of the teeth at least once a day, at least once every two days, at least once every three days, at least once every five days, at least once a week, at least once every two weeks, or at least once a month. The oral care product and/or the whitening composition thereof may be utilized for up to 2 weeks, up to 3 weeks, up to 4 weeks, up to 6 weeks, up to 8 weeks, or greater.

The dental tray may be of any conventional form, and may be formed from conventionally used polymers, such as thermoplastic polymers. Thermoset polymers also may be used. Accordingly, the dental tray may range from highly flexible to a low flexibility. The thermoplastic polymers are typically used. Illustrative thermoplastic polymers may be or include, but are not limited to, polyethylene and polypropylene polymers, their derivatives and copolymers, silicone elastomers, polyurethanes and derivatives, polycaprolactams, polystyrene and derivatives, polybutadiene and derivatives, polyisoprene and derivatives, and polymethacrylate and its derivatives, or the like, or combinations thereof.

All ingredients for use in the compositions described herein should be orally acceptable. As used herein, "orally acceptable" may refer any ingredient that is present in a composition as described in an amount and form that does not render the composition unsafe for use in the oral cavity.

EXAMPLES

The examples and other implementations described herein are exemplary and not intended to be limiting in describing the full scope of compositions and methods of this disclosure. Equivalent changes, modifications and variations of specific implementations, materials, compositions and methods may be made within the scope of the present disclosure, with substantially similar results.

Example 1

The whitening efficacy of a control gel whitening composition (4) and three test gel whitening compositions (1)-(3) for whitening teeth was evaluated. Each of the control and test whitening compositions (1)-(4) was prepared by combining the components/ingredients according to Table 1. As indicated in Table 1, the control whitening composition (4) included about 0.1 weight % hydrogen peroxide, and the test whitening compositions (1)-(3) included 0.1 weight % hydrogen peroxide in combination with varying amounts of a salt of peroxymonosulfate, namely potassium peroxymonosulfate (MPS). Particularly, the test whitening compositions (1), (2), and (3) included about 1 weight %, about 3 weight %, and about 5 weight % of MPS. The control whitening composition (4) represented a commercially available whitening gel product.

TABLE 1

Composition of Control and Test Whitening Compositions (1)-(4)

| Ingredient | (1) | (2) | (3) | (4) |
|---|---|---|---|---|
| Silicone Fluid (wt %) | 50 | 50 | 50 | 48.1 |
| Fumed Silica (wt %) | 2 | 3 | 1 | 1 |
| MPS (~50% active solid) (wt %) | 2 | 6 | 10 | — |
| (PEG)-(PG)-(PEG) Block Copolymer (wt %) | 38.25 | 35.25 | 33.25 | — |
| Anticalculus Agent (wt %) | 3 | 2 | 2 | — |
| Polyvinyl Pyrrolidone (wt %) | 3 | 2 | 2 | 24.35 |
| PVP-Hydrogen Peroxide (wt %) | 0.55 | 0.55 | 0.55 | 0.55 |
| Antimicrobial Agent (wt %) | 0.1 | 0.1 | 0.1 | 0.1 |
| Flavoring Agent (wt %) | 1.1 | 1.1 | 1.1 | 0.9 |
| White Petrolatum (wt %) | — | — | — | 25 |
| Total | 100 | 100 | 100 | 100 |

To evaluate the whitening efficacy of the control and test whitening compositions (1)-(4), bovine teeth stained with a tobacco solution and having L* values of about 60 were obtained. A total of four teeth were used to evaluate each of the control and test whitening compositions (1)-(4). To evaluate the whitening efficacy, each of the bovine teeth were treated with 14 whitening cycles. Each whitening cycle included applying about 50 mg of each of the control and test whitening compositions (1)-(4) to respective surfaces of the bovine teeth, soaking the teeth in a circulated system containing a phosphate buffer maintained at a pH of about 7 for about 15 minutes, removing the control and test gel whitening compositions (1)-(4) and the buffer from the surfaces of the bovine teeth, and thoroughly drying the bovine teeth.

The L*, a*, b* values were measured with a hand-held spectrophotometer (SPECTROSHADE Micro instrument manufactured by Medical High Technology of Verona, Italy). The L*, a*, b* values were compared to baseline values measured before treatment to calculate the change in the whiteness of each of the bovine teeth. It should be appreciated that the whiteness index (W*) is a measure of overall color change relative to pure white, and is given by formula (1), and the change in whiteness index (ΔW*) is measured by formula (2). It should further be appreciated that the lower the whiteness index (ΔW*) the whiter the teeth. The change in whiteness index (ΔW*), or whitening efficacy, is summarized in Table 2.

$$W^* = ((L^*-100)^2 + (a^*)^2 + (b^*)^2)^{1/2} \quad (1)$$

$$\Delta W^* = W^*_{treated} - W^*_{baseline} \quad (2)$$

TABLE 2

Whitening Efficacy (ΔW*) of Control And Test Whitening Compositions (1)-(4)

| | | Number of Treatments | | | | | |
|---|---|---|---|---|---|---|---|
| | | 0 | 1 | 2 | 4 | 8 | 14 |
| (1) 0.1 wt % HP & 1 wt % MPS | ΔW* Std. Dev. | 0 0 | −1.56 0.56 | −2.29 0.47 | −3.29 0.59 | −4.75 0.83 | −5.70 1.042 |
| (2) 0.1 wt % HP & 3 wt % MPS | ΔW* Std. Dev. | 0 0 | −0.95 0.22 | −1.63 0.19 | −2.80 0.45 | −4.42 0.16 | −5.78 0.53 |
| (3) 0.1 wt % HP & 5 wt % MPS | ΔW* Std. Dev. | 0 0 | −1.41 0.26 | −2.36 0.13 | −3.96 0.22 | −5.63 0.47 | −6.99 0.54 |
| (4) 0.1 wt % HP | ΔW* Std. Dev. | 0 0 | −0.019 0.11 | −0.19 0.19 | −0.49 0.17 | −0.71 0.23 | −1.06 0.16 |

As illustrated in Table 2, the test gel whitening compositions (1)-(3) all exhibited relatively greater whitening efficacy in removing hard to remove stains, such as tobacco stains, as compared to the control gel whitening composition (4) which only included hydrogen peroxide.

The present disclosure has been described with reference to exemplary implementations. Although a limited number of implementations have been shown and described, it will be appreciated by those skilled in the art that changes may be made in these implementations without departing from the principles and spirit of the preceding detailed description. It is intended that the present disclosure be construed as including all such modifications and alterations insofar as they come within the scope of the appended claims or the equivalents thereof.

What is claimed is:

1. An oral care composition, comprising:
   an orally acceptable vehicle;
   a whitening booster dispersed in the orally acceptable vehicle, wherein the whitening booster comprises potassium peroxymonosulfate in an amount of 1% to 5% by weight of the composition; and
   a source of hydrogen peroxide; wherein the source of hydrogen peroxide is cross-linked polyvinylpyrrolidone (PVP) hydrogen peroxide complex present in an amount to provide 0.1% hydrogen peroxide by weight of the composition;
   wherein the oral care composition is a tooth whitening gel.

2. The oral care composition of claim 1, wherein the whitening booster consists essentially of the salt of the monopersulfate, optionally the whitening booster consists of the salt of the monopersulfate.

3. The oral care composition of claim 1, wherein the whitening composition prior to use is substantially free of water.

4. The oral care composition of claim 1, wherein the orally acceptable vehicle comprises a structure-building agent.

5. The oral care composition of claim 4, wherein the structure-building agent comprises an amphiphilic copolymer, optionally, the amphiphilic copolymer comprises a polyvinylpyrrolidone vinyl acetate copolymer.

6. The oral care composition of claim 4, wherein the structure-building agent comprises a poloxamer, optionally, the poloxamer comprises a poly(ethylene glycol)-block-poly(propylene glycol)-block-poly(ethylene glycol).

7. A method for whitening teeth of a subject, comprising contacting the oral care composition of claim 1 with a surface of the teeth of the subject in need thereof.

8. The method of claim 7, wherein contacting the oral care composition with the surface of the teeth comprises directly applying the oral care composition with a delivery device, optionally, the delivery device is an applicator comprising a brush, a roller ball, or a felt tip.

9. The method of claim 7, wherein contacting the oral care composition with the surface of the teeth comprises disposing the oral care composition in a dental tray, and disposing the dental tray about the teeth.

10. The method of claim 7, wherein the oral care composition is contacted with the surface of the teeth for at least 5 minutes, optionally, at least 10 minutes, further optionally, at least 15 minutes.

\* \* \* \* \*